(12) United States Patent
Ibragimov (10) Patent No.: US 9,839,768 B2
(45) Date of Patent: Dec. 12, 2017

(54) INTRODUCER CATHETER WITH A ROTATING NEEDLE TO OBTAIN VASCULAR ACCESS (71) Applicant: Araz Ibragimov, Brooklyn, NY (US)

(72) Inventor: Araz Ibragimov, Brooklyn, NY (US)

( * ) Notice: Subject to any disclaimer, the term of this patent is extended or adjusted under 35 U.S.C. 154(b) by 776 days.

(21) Appl. No.: 14/262,959

(22) Filed: Apr. 28, 2014

(65) Prior Publication Data
US 2015/0305769 A1 Oct. 29, 2015

(51) Int. Cl.
A61B 17/34 (2006.01)
A61M 25/06 (2006.01)

(52) U.S. Cl.
CPC ...... *A61M 25/065* (2013.01); *A61M 25/0606* (2013.01); *A61M 25/0693* (2013.01)

(58) Field of Classification Search
CPC .............. A61M 25/06; A61M 25/0662; A61M 25/0693; A61M 2025/0681; A61B 17/3415; A61B 17/3417
See application file for complete search history.

(56) References Cited

U.S. PATENT DOCUMENTS

| 4,850,960 | A | 7/1989 | Grayzel | |
| 5,423,770 | A * | 6/1995 | Yoon | A61B 17/3417 604/158 |
| 5,938,635 | A | 8/1999 | Kuhle | |
| 7,419,496 | B2 * | 9/2008 | Staudner | A61B 17/3496 606/185 |
| 7,549,996 | B2 | 6/2009 | Vaisman | |
| 2007/0016164 | A1 | 1/2007 | Dudney | |
| 2012/0095447 | A1 | 4/2012 | Fojtik | |
| 2012/0253274 | A1 * | 10/2012 | Karlsson | A61M 5/2033 604/89 |
| 2013/0150793 | A1 | 6/2013 | Beissel | |
| 2014/0039534 | A1 * | 2/2014 | Geist | A61B 17/3472 606/172 |
| 2014/0052021 | A1 | 2/2014 | Burkholz | |
| 2014/0088509 | A1 * | 3/2014 | Sonderegger | A61M 25/0631 604/157 |

FOREIGN PATENT DOCUMENTS

| WO | 89/00060 | 1/1989 |
| WO | 2003024517 | 3/2003 |

OTHER PUBLICATIONS

Kuensting LL et al. Difficult venous access in children: taking control. Journal of emergency nursing, Sep. 2009, pp. 419-424.
Lininger RA. Pediatric peripheral i.v. insertion success rates. Pediatric Nursing. Sep.-Oct. 2003 29(5):351-4. Abstract only.

* cited by examiner

*Primary Examiner* — Matthew F Desanto
(74) *Attorney, Agent, or Firm* — Boris Leschinsky (57) ABSTRACT An introducer catheter for obtaining access to a blood vessel includes a hollow needle with a beveled tip extending from a needle hub as well as a flexible sheath slidingly positioned over the needle. The needle hub includes an actuator configured to rotate the needle tip by about ½ of a turn upon reaching the target vessel. Rotation of the needle tip allows a more confident motion of advancing the sheath further into the vessel to secure the sheath therein. The introducer catheter of the invention is designed to increase success rate of vessel access using minimal number of needle punctures and to decrease the rate of vascular complications, especially in vulnerable patients such as children.

10 Claims, 6 Drawing Sheets

INTRODUCER CATHETER WITH A ROTATING NEEDLE TO OBTAIN VASCULAR ACCESS

BACKGROUND OF THE INVENTION

The present invention relates generally to introducer catheters. More particularly, the invention describes a catheter with a needle capable of rotating around its longitudinal access for about ½ of a turn once blood back event is obtained indicating that the needle has entered the target vessel. Rotation of the needle is done to facilitate catheter introduction into the target vessel.

Establishing vascular access is one of the most common procedures carried out in the emergency department and other locations in the hospital as out in the field. This procedure is a high priority for the care of a critically ill and unstable patient. The condition of the patient often plays a role in the likelihood of attaining vascular access. Conditions associated with difficult vascular access include obesity, chronic illness, hypovolemia, intravenous drug abuse, and vasculopathy. Patients with difficult intravenous (IV) access are frequently subjected to repeated attempts by multiple practitioners.

Success rate and time to vascular cannulation are crucial to the optimal resuscitation of a critically-ill patient. This can be challenging to even the most experienced medical personnel. Failure rates of emergent IV access vary in the literature ranging from 10 to 40%. The average time requirement for peripheral IV cannulation is reported at 2.5 to 13 minutes, with difficult IV access requiring as much as 30 minutes. The number of attempts at IV cannulation for the pediatric patient ranges from 1 to 10 attempts making this patient population especially challenging.

Central venous catheterization (CVC) is a common alternative approach to attain cannulation in patients with difficult venous access. CVC cannulation provides vascular access for fluid resuscitation, and additionally allows for hemodynamic monitoring. It is noted, however, that CVC cannulation presents additional risks to the patient. Most common among these complications are venous thrombosis, arterial puncture, catheter associated bloodstream infection, and pneumothorax.

Given the time required to establish a central venous catheter, the increased risk to the patient, and the skill required of the provider, there is an unmet need for improved devices and methods facilitating rapid and reliable vascular access, especially for less-trained medical personnel.

SUMMARY OF THE INVENTION

Accordingly, it is an object of the present invention to overcome these and other drawbacks of the prior art by providing a novel introducer catheter configured to increase the likelihood of obtaining and retaining vascular access with minimum number of attempts, most of the time using a single attempt.

It is another object of the present invention to provide a novel introducer catheter configured to minimize vessel damage caused by multiple needle punctures or double wall penetration.

It is a further object of the present invention to provide a novel introducer catheter configured to minimize the need for training of medical personnel in a procedure to obtain vascular access.

It is yet a further object of the present invention to provide a novel adapter for a standard introducer catheter configured to improve success rate of obtaining vascular access with minimum number of attempts.

The novel introducer catheter of the invention comprises a hollow needle extending from a needle hub. The hollow needle may be made from stainless steel and terminated with a beveled tip. The introducer catheter further comprises a sheath extending from a sheath hub over the hollow needle. The distal end of the sheath may be located adjacent to the beveled tip of the hollow needle. The sheath may in turn extend from a sheath hub removably retained on the needle hub. Importantly, the needle hub includes an actuator configured to cause the hollow needle to rotate about ½ of a turn upon activation thereof. Such actuation may be achieved using spring-loaded or manually-activated mechanisms described in further detail below. Rotating the beveled tip once inside the target vessel allows avoiding double wall puncture while advancing the sheath into the vessel, which therefore may improve the success rate of the procedure.

Also described are designs for a novel adapter configured to be attached to a standard introducer sheath to convert it to a design allowing convenient ½ turn rotation of the hollow needle once its beveled tip is placed inside the target vessel.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 1b is a general side view of a subsequent stage of the procedure shown in FIG. 1a;

FIG. 4b is a variation of the novel method as described in FIG. 4a;

FIG. 12b shows a side view of the novel adapter aligned with the introducer catheter of FIG. 12a;

DETAILED DESCRIPTION OF THE PREFERRED EMBODIMENT OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The term "vessel" is used throughout this description to include various blood vessels such as venous and arterial vessels, as well as other internal cavities and voids both fluid-filled and not fluid-filled that may be accessed by inserting a catheter. The terms "vascular access" and "vessel access" are used interchangeably. The term "introducer catheter" is used herein to include any device that uses a puncture tool to access a target vessel followed by sliding a tube into the vessel and removal of the puncture tool to allow subsequent vessel access. Arterial and venous introducer catheters and sheaths are some examples of these devices. Another example is a trocar that may be used during a minimally invasive surgery. Such devices may include provisions for a guide wire or have no guide wire. The term further includes devices configured to access the vessel by puncturing and penetrating the skin, as well as those that are configured to access the vessel by puncturing and traversing through other body tissues and orifices.

Figure 1A:
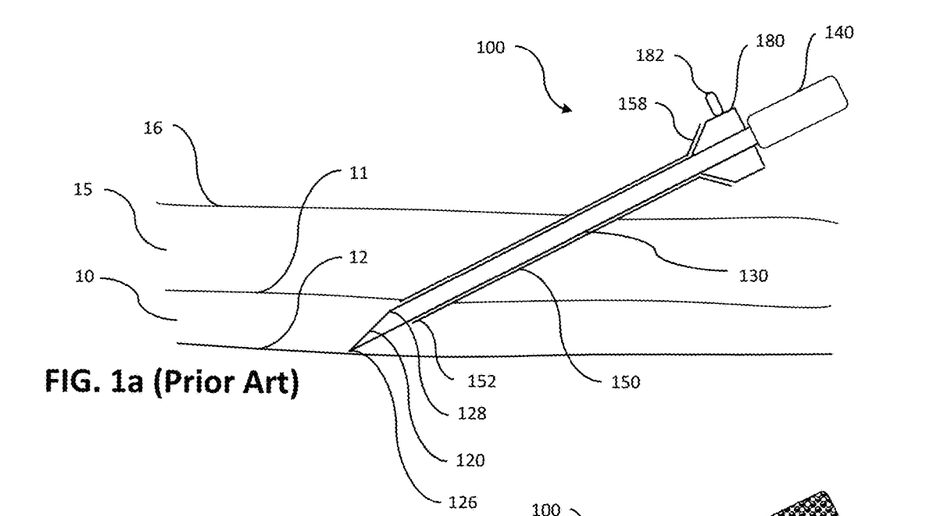
FIG. 1a is a general side view of the first stage in a traditional procedure of gaining vessel access using a commonly known design of an introducer catheter.

A traditional procedure of accessing a target vessel is depicted generally in FIG. 1a, which shows a target vessel 10 having an anterior vessel wall 11 and a posterior vessel wall 12 located within tissue layer 15 under a skin layer 16. A commonly known introducer catheter 100 is shown inserted through the skin 16 and into the vessel 10. The introducer catheter 100 includes a hollow needle 130 extending from a needle hub 140 to a beveled tip 120. The needle hub may include a transparent visualization chamber to indicate when the needle tip 126 enters the target vessel by the entry and presence of blood inside the visualization chamber. A flexible sheath 150 may be slidingly positioned over the hollow needle 130 extending from a sheath hub 158 to a distal sheath end 152 located adjacent the proximal end 128 of the beveled tip 120. The sheath hub 158 may include a cavity formed for example as a luer fitting for subsequent attachment of the fluid infusion line thereto once the procedure of obtaining vessel access is complete. A sliding pusher 180 with a protruding slider 182 may be positioned over the hollow needle 130 and adapted to facilitate advancement of the sheath 150 into the target vessel once the needle has reached it as evident from the presence of blood in the visualization chamber of the needle hub 140.

Figure 1B:
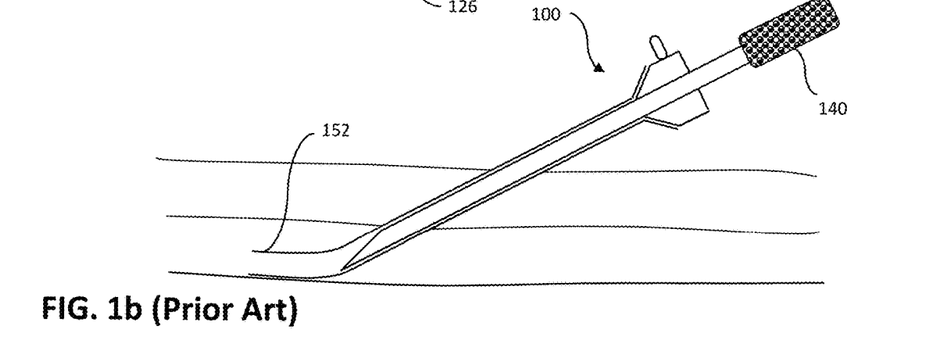
Figure 1C:
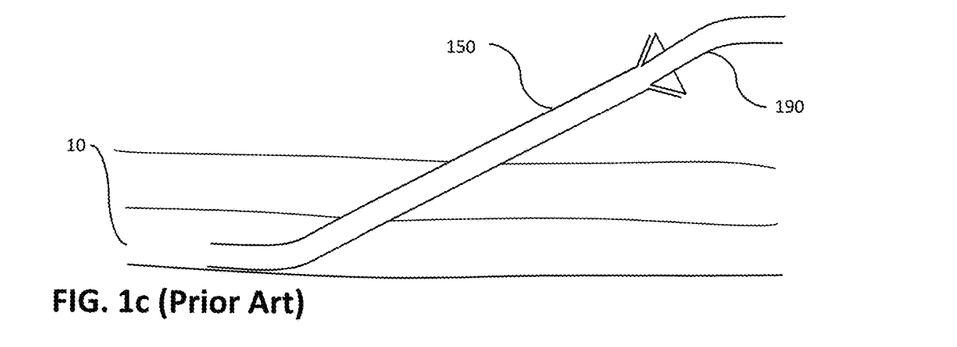
FIG. 1c is a general side view of the final stage of the procedure of gaining vascular access shown in previous figures.

In a typical procedure of obtaining vascular access, the introducer catheter 100 is inserted through the skin 16 at a shallow angle to the vessel 10 until the beveled tip 120 reaches the vessel by penetrating the anterior vessel wall 11, as seen in FIG. 1a. Blood pressure may be sufficient in this case to force blood from the vessel 10 up the hollow needle 130 and into the visualization chamber inside the needle hub 140. Once the blood is observed inside the needle hub 140 as illustrated in FIG. 1b, the sheath 150 may be moved forward by sliding the pusher 180 off the needle hub 140 so that the distal end 152 of the sheath 150 is located deeper in the target vessel 10. At this point, the needle 130 and the pusher 180 may be removed and the fluid infusion line 190 may be attached to the sheath hub, see FIG. 1c.

Figure 2:
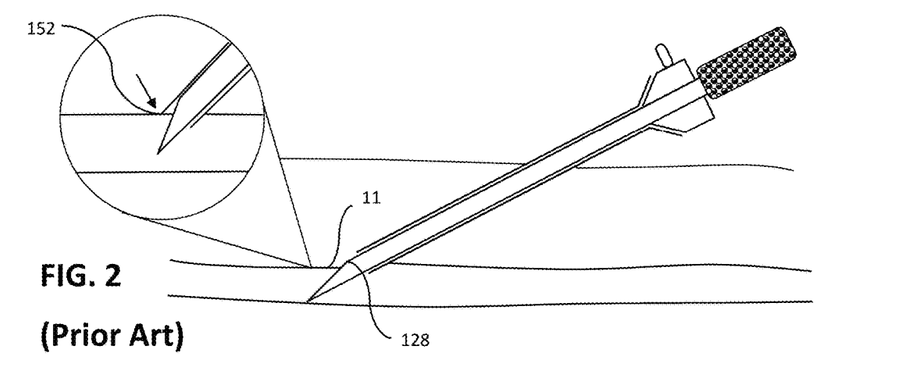
FIG. 2 shows schematically one set of circumstances causing complications during the procedure to obtain vascular access.

Although the above described device and approach may work well for many patients, there may be various circumstances when a difficulty of one type or another may be encountered. One such situation is shown in FIG. 2, in which a smaller caliber vessel is penetrated by a larger hollow needle 130 with a sizable beveled tip 120. In this case, while the distal end 126 of the needle tip is inside the vessel 10, its proximal end 128 may be outside the anterior wall 11 and in the tissue layer 15. The same situation may be encountered with any side vessel 10 or hollow needle 130 when the tip 120 is not inserted deep enough through the anterior wall 11. Attempts to advance the distal tip 152 of the sheath 150 through the anterior vessel wall 11 may cause bunching up the distal end 152 as a result of not being inside the vessel 10—and subsequent vessel trauma, see insert in FIG. 2.

Figure 3:
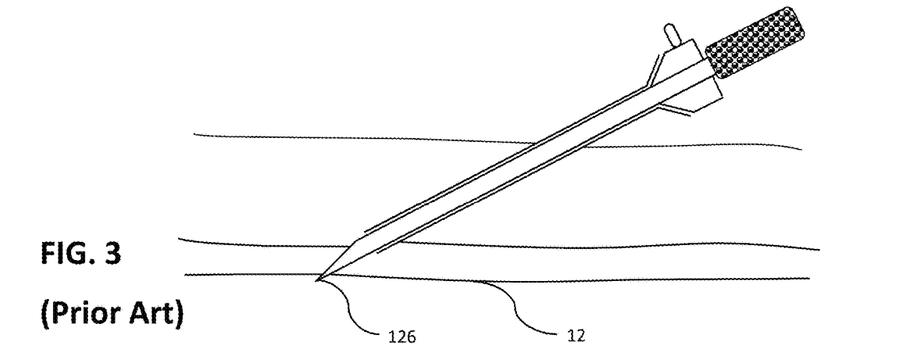
FIG. 3 shows another set of circumstances causing other complications during the procedure of obtaining vascular access as depicted above.

Another set of circumstances which may present a difficulty for a medical practitioner and cause vessel damage is double wall puncture of both the anterior vessel wall 11 and the posterior vessel wall 12 by the tip 120 of the hollow needle 130, see FIG. 3. Although blood may still be present in the visualization chamber in the needle hub 140, attempts to advance the sheath 150 into the vessel 10 may encounter resistance at the bottom of the vessel where the distal end 126 of the tip 120 may preclude easy advancement of the sheath 150 into the vessel 10.

Figure 4A:
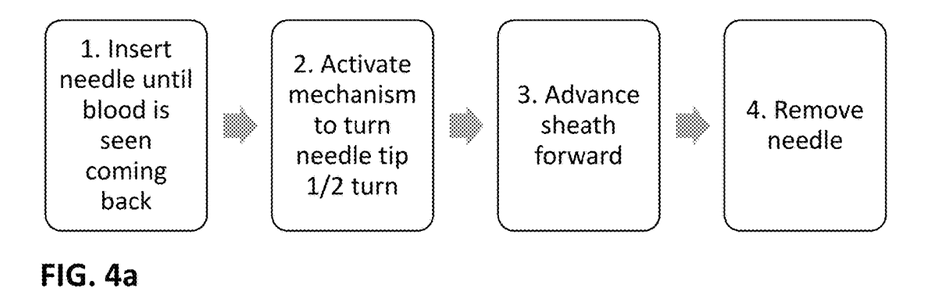
FIG. 4a is a general block-diagram of the steps of the novel method of gaining vascular access involving rotation of the needle once its tip is placed inside the target vessel.
Figure 4B:
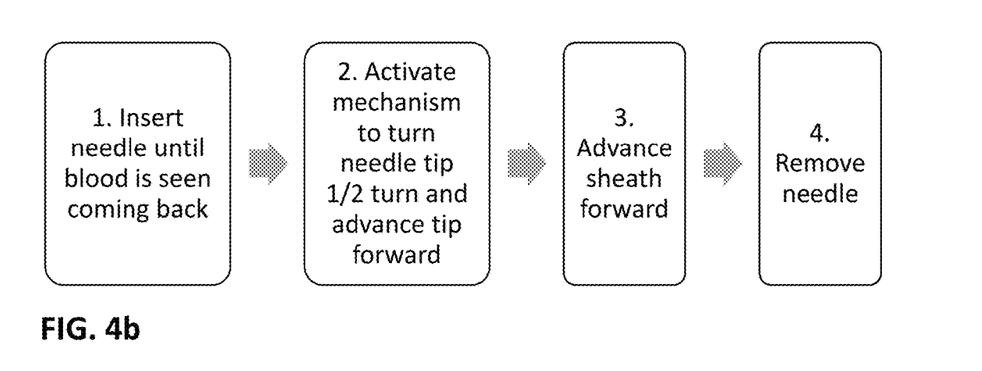

According to methods of the invention shown schematically in FIGS. 4a and 4b, the novel introducer catheter may be configured to perform the following steps:

1. Insert the hollow needle 130 until the tip 120 is confirmed to reach the internal space of the target vessel 10, for example by observing blood coming back from the hollow needle 130, and optionally into the visualization chamber in the needle hub 140. In embodiments where no visualization chamber is present, blood exiting the hub of the hollow needle may be used as this indication;
2. Activate a mechanism to turn the tip 120 of the hollow needle 130 about ½ of a turn. A more detailed explanation of the effects of such rotation of the tip 120 are explained below;
3. Advance the sheath 150 of the introducer catheter forward into the vessel 10; and
4. Remove the hollow needle 130.

As opposed to pure rotation of the tip 120 in the method illustrated in FIG. 4a, the method illustrated in FIG. 4b adds its longitudinal advancement along with the distal tip 152 of the sheath forward into the vessel 10. In embodiments, this advancement of the needle tip and the sheath over it may first be preceded by advancing the distal end of the sheath to cover the cutting edge of the needle tip so as to protect the vessel from unintended trauma during subsequent advancement of the assembly of the needle and the sheath.

Figure 5A:
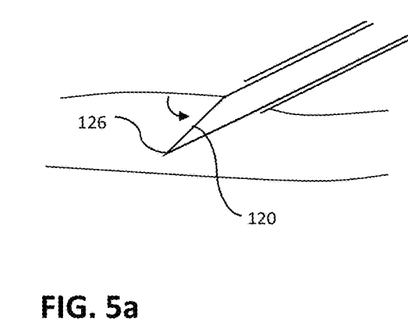
FIG. 5a shows the details of the beveled tip of the hollow needle after insertion into the target vessel according to the new method.
Figure 5B:
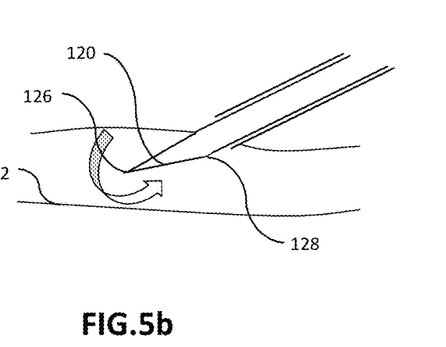
FIG. 5b shows the same after rotating the tip about ½ of a turn.

Half-turn rotation of the beveled tip 120 of the hollow needle 130 once inside the target vessel 10 has a number of beneficial effects for the remaining steps of the procedure of obtaining vascular access. As can be seen in FIG. 5a, the distal end 126 of the needle tip 120 is very sharp and has a risk of double wall puncture as shown above in FIG. 3. When the tip 120 is rotated about ½ of a turn (see FIG. 5b), the flat edge of the bevel aligns generally parallel with the vessel wall 12. In that position, further pushing down of the hollow needle 130 may not cause as much damage to the vessel 10. Also notable is the higher position of the distal end 126 inside the vessel 10 and an increased distance between thereof and the posterior wall 12—further reducing the risk of double wall puncture and providing more room for the sheath 150 to be advanced into the vessel 10. In addition, even if the distal end 126 had accidentally penetrated through the posterior wall 12, rotation of the hollow needle 130 may likely bring it back inside the vessel 10 so that the subsequent advancement of the sheath 150 into the vessel may proceed with reduced risk of vessel damage. Finally, in case of small diameter vessels of inadequate penetration by the hollow needle 130 of the anterior vessel wall 11 (as described above and shown in FIG. 2), rotation of the hollow needle will provide increased support for advancement of the sheath 150 into the vessel 10.

Figure 5C:
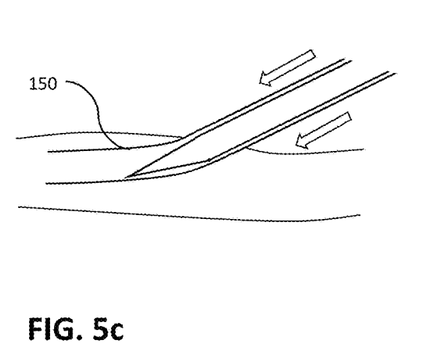
FIG. 5c shows the same after advancing the sheath deeper into the target vessel.
Figure 5D:
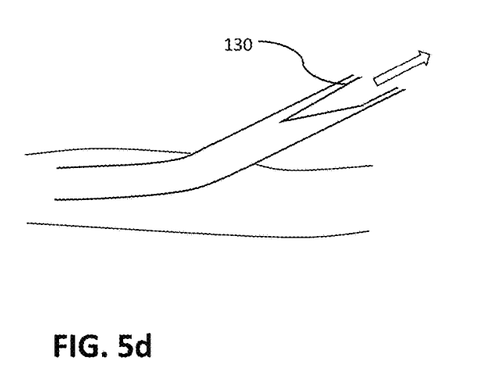
FIG. 5d shows the same with the hollow needle being removed.

Following step 2 of the method of rotating the hollow needle 130 by about ½ of a turn, the procedure may be continued to the step of advancing the sheath 150 into the vessel 10 as seen in FIG. 5c and further to needle removal as seen in FIG. 5d.

For the purposes of this description, the term "½ of a turn" referring to rotation of the tip 120 of the hollow needle 130 includes a broad range of rotation angles from 120 degrees to 240 degrees.

First Embodiment of the Present Invention

Figure 6:
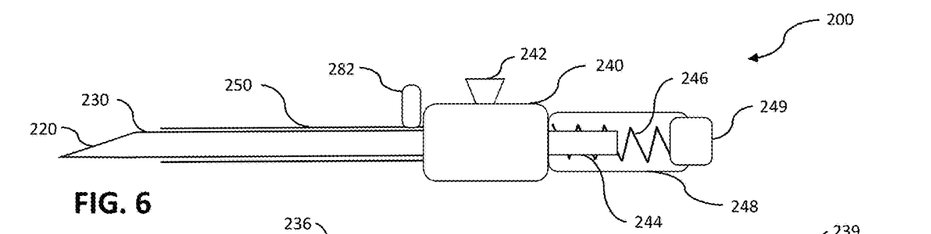
FIG. 6 is a general side view of the novel introducer catheter according to the first embodiment of the present invention.

Various devices of the first embodiment 200 of the present invention are generally depicted in FIGS. 6 through 11. FIG. 6 shows a general side cross-sectional view of the first embodiment of the invention. A hollow needle 230 may be used for the introducer catheter of the invention, the hollow needle having a design similar to that of traditional hollow needles suitable for percutaneous punctures. The hollow needle 230 may for example be made from medical grade stainless steel or another suitable material and comprise a tube sized to be from 12 gauge to 30 gauge. The distal end of the hollow needle may have a straight beveled tip 220 or a beveled tip with a compounded shape, for example using one of the designs described in the US Patent Publication No. 2008/0154217 by Carrez or U.S. Pat. No. 7,549,996 by Vaisman, both of which are incorporated herein in their respective entireties by reference. The bevel of the tip 220 may be made at an acute angle from 10 degrees to 45 degrees or another angle suitable for a particular application.

The hollow needle 230 may be made to extend from a needle hub 240 containing an actuator configured to turn the needle by about ½ of a turn as described below in more detail.

Movably positioned over the hollow needle 230 is a flexible sheath 250 extending from a sheath hub 282, which in turn may be equipped with a protrusion allowing the sheath to be disengaged from the needle hub 240 and slidingly moved along the needle 230 when inserting into the target vessel. In alternate designs of the invention (not showed), the sheath hub may include a luer fitting removably attached to a sliding pusher 180 similar to the design depicted and described above.

Figure 7:
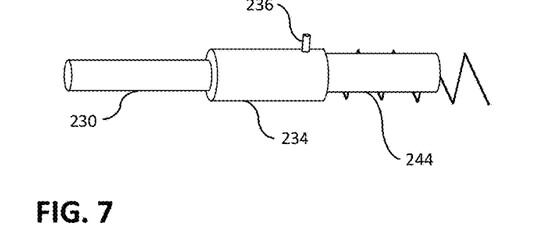
FIG. 7 shows the details of the internal mechanism of the catheter shown in FIG. 6.
Figure 8:
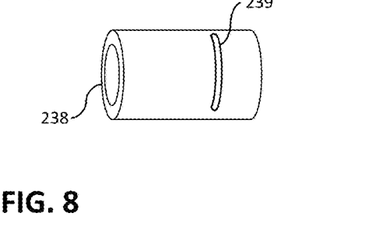
FIG. 8 shows the external cylinder as part of the mechanism of the introducer catheter shown in FIG. 6.
Figure 9A:
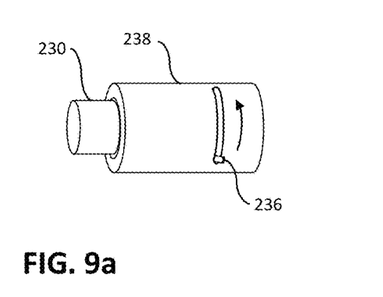
FIG. 9a shows an internal cylinder inside the external cylinder in a first position.
Figure 9B:
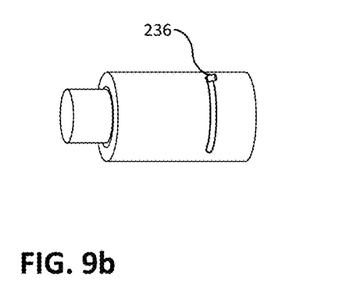
FIG. 9b shows the same in a second position

The actuator for rotating the hollow needle 230 generally includes trigger 242 and a spring-loaded rotating mechanism, which in turn may include an internal cylinder 234 sized to be rotatably retained inside an external cylinder 238—as seen in FIGS. 6-8. The hollow needle 230 may be aligned with and attached to the internal cylinder 234, while the external cylinder 238 may be attached to or formed together with a housing of the needle hub 240. Both the internal cylinder 234 and the external cylinder 238 may be located inside the housing of the needle hub 240. In embodiments, a pin 236 may be radially extending outwards from the internal cylinder 234 and configured to slide inside a groove 239 formed in the external cylinder 238. In other embodiments (not shown), the pin 236 may be extending inwards from the external cylinder 238 and configured to slide in the groove 239 formed in the internal cylinder 234). The pin 236 and the mating groove 239 may be configured to limit the angle of rotation of the internal cylinder 234 inside the external cylinder 238 by about ½ of a turn when the pin 236 travels from one end of the groove 239 to the other end thereof. Other alternate mechanical approaches configured to limit the angle of rotation of needle 230 inside the needle hub 240 may be used for the purposes of the invention as may be easily appreciated by those skilled in the art. The groove 239 shown in FIG. 8 is extending radially around the external cylinder 238 and is designed to cause rotation of the internal cylinder 234 while the pin 236 is moving inside thereof—see FIGS. 9a and 9b showing the initial and the final position of the pin 236 inside the groove 239.

Figure 10:
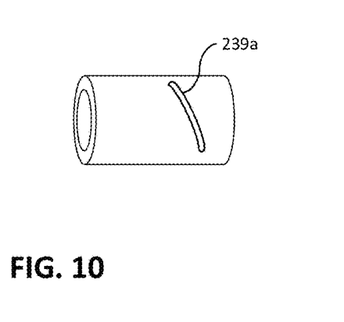
FIG. 10 shows one example of groove design in the external cylinder allowing the hollow needle to be advanced forward during its rotation.
Figure 11:
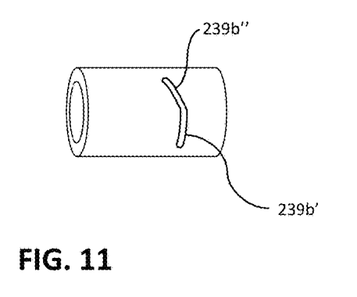
FIG. 11 shows another example of groove design configured for the same purpose.

Alternate designs of the groove 239 are shown in FIGS. 10 and 11. According to the method of the invention shown in FIG. 4b, the rotation of the needle 230 may be accompanied by a slight forward movement thereof along with the sheath 250. The need to advance the tip of the needle 220 and the distal end of the sheath 250 may be dictated by a small distance between the distal end of the sheath 250 and the beginning of the bevel of the hollow needle tip 220.

Typically, such distance is between 1 to 3 mm. rotating the needle alone without this small advancement forward into the vessel may not position the distal end of the sheath 250 inside the vessel 10. Addition of this short forward movement of the needle tip 220 may be used to assure confident placement of the sheath through the anterior wall 11 and into the internal passage of the target vessel 10. To accomplish this movement, the groove 239a as seen in FIG. 10 may be made to be not radially going around the cylinder 238 but include with a small diagonal angle such that the initial position of the pin 236 inside thereof is axially spaced apart from the final position of the tip by 1-3 mm, with the final position of the tip being further distal towards the vessel as compared with the initial position.

Other shapes of the groove may further be used to cause both rotation and axial advancement of the needle tip 220. One such example is seen in FIG. 11—the groove 239b has a first portion 239b' being radial and the second portion 239b" having a diagonal incline forward towards the distal end of the needle 230. Using such groove will cause the tip 220 to first turn about ¼ of a turn and then both continue to turn the remaining ¼ of a turn while advancing forward by a distance between 1 and 3 mm—to assure placement of the sheath inside the target vessel 10.

The spring-loaded rotating mechanism described above may be actuated (released to cause needle rotation) by depressing a trigger 242 based on a biased spring 246 causing rotation of the internal cylinder 234. The spring 246 may have one end operatively connected to the internal cylinder 234 and the other end operatively connected to the external cylinder 238 so that winding up and then releasing the spring 246 may cause the internal cylinder 234 to rotate inside the external cylinder 238. The spring 246 may be pre-wound at the factory or can be wound up to a preloaded state before using the device of the invention, for example by manually rotating the winding knob 249. The spring 246, the knob 249 and the optional visualization chamber (assembled in fluid communication with the hollow needle 230) may be positioned inside a transparent housing 248 extending from the needle hub 240. The trigger 242 may have a protrusion (not shown) configured to prevent rotation of the needle until activation of the actuator of the invention.

In use, the device 200 may first be used to place the needle tip 220 into the target vessel 10 as may be confirmed for example by the presence of blood in the visualization chamber 244. The trigger 242 may then be pressed to cause activation of the actuator leading to an automatic rotation (optionally coupled with a short forward advancement) of the needle tip 220 by about 180 degrees. At this point, the sheath hub 282 may be disengaged from the needle hub 240 and the sheath 250 may be further advanced into the vessel as described above. As compared to the traditional procedure of gaining access to the target vessel, the device 200 of the invention allows to conveniently benefit from the needle tip rotation without the need for extensive personnel training as the rotation is done automatically by depressing the trigger 242.

Figure 12A:
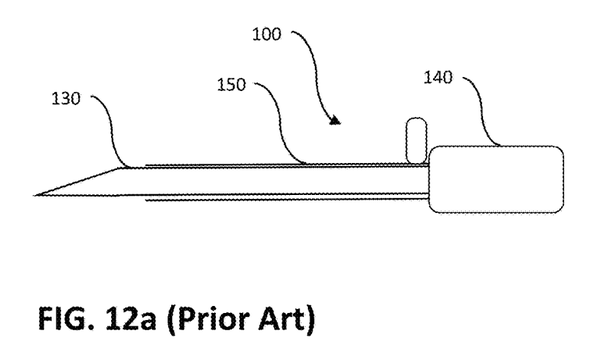
FIG. 12a shows a side view of standard introducer catheter.
Figure 12B:
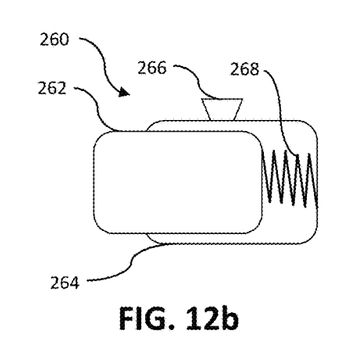

In further embodiments, the concepts described above for a device 200 may be implemented for use with traditional introducer catheter 100 depicted in FIG. 12a. In this case, an adapter 260 is proposed (as seen in FIG. 12b), which may include an adapter housing 264 and an internal sleeve 262 rotatably supported inside the adapter housing 264. The internal sleeve 262 may be configured to removably engage with the needle hub, for example by having a compressible sleeve inside thereof sized to snugly go over the needle hub.

The adapter housing 264 may further comprise an actuator configured to cause the internal sleeve 262 to rotate about ½ of a turn upon actuation thereof. The adapter housing 264 may be made transparent or contain a transparent window so as to allow observation of the visualization chamber, which may be located inside the needle hub.

The adapter 260 may include a spring-loaded actuator similar to the design described above for the device 200 including a spring 268 operatively connected both to the adapter housing 264 and the internal sleeve 262, wherein upon activation of the actuator the spring causes the internal sleeve 262 to rotate inside the adapter housing 264.

Similar to the above described device 200, the internal sleeve 262 (or the adapter housing 264 may include a pin positioned inside a groove (not shown) formed in a respectively another of the adapter housing 264 or the internal sleeve 262, the groove shaped to limit the rotation of the internal sleeve 262 by about ½ of the turn. The adapter 260 may further comprise a trigger 266 configured to activate the actuator upon depressing thereof—similar to the trigger 242.

Figure 13:
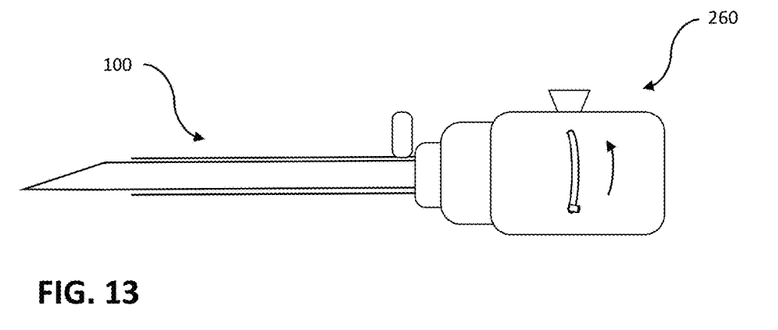
FIG. 13 shows the novel adapter assembled over the standard introducer catheter of the prior art.

In use, the adapter 260 may be first placed over the needle hub 140 as seen in FIG. 13. The assembly of the adapter 260 and the introducer 100 may then be used to obtain the initial puncture of the vessel, followed by depressing of the trigger 266—which leads to activation of the spring-loaded actuator and rotation of the needle tip by ½ of a turn. The sheath 150 may then be disengaged from the needle hub 140 and advanced further into the vessel 10, followed by removal of the needle 150 and the adapter 260 from the sheath 150.

Second Embodiment of the Present Invention

Figure 14:
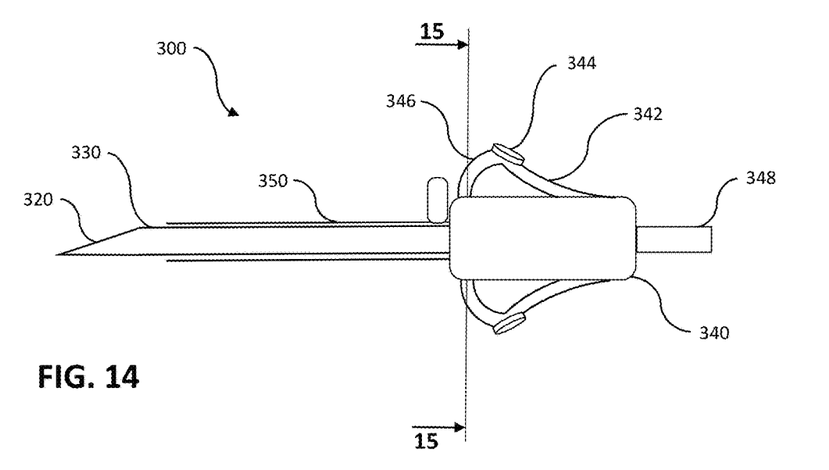
FIG. 14 shows a side view of a second embodiment of the novel introducer catheter according to the present invention.

A second embodiment of the present invention is generally depicted in FIG. 14 with various additional views presented in FIGS. 15-18. Shown in FIG. 14 is a side view of the device 300 comprising a hollow needle 330 of the design similar to that shown for the device 200 described above. The hollow needle may have a distal end with a beveled tip 320. The hollow needle 330 extends from a needle hub 340 described in greater detail below.

A flexible sheath 350 slidingly extends over the hollow needle 330 from a sheath hub which is removably attached to the needle hub 340. The flexible sheath 350 extends distally to a location close to the beginning of the bevel cut of the tip 320. The space between the end of the sheath 350 and the beginning of the tip 320 may be as little as 1-3 mm.

The needle hub 340 contains an actuator capable of rotating the needle 330 by about ½ of a turn upon depressing two manually-operable buttons 344 positioned symmetrically on both sides of the needle hub 340. The location and design of the manually-operable buttons 344 may be selected to allow both a retention and operation of the needle hub with two fingers during the advancement of the hollow needle 330 through the skin and into the vessel 10, as well as activation of the actuator upon depressing thereof—all without the need to change the grip of the device 300. This configuration may be advantageous so as not to disturb the position of the needle tip 320 once in the vessel 10.

Each button 344 may be placed at the end of the arm 342, which in turn may be attached to the needle hub 340 and configured to allow inward movement of the button 344. This may be done using a rotation of the arm around the axis at the place of attachment to the needle hub 340 or by making the arm 342 resilient and flexible so as to allow it to flex inward upon depressing of the button 344.

In embodiments, two manually-operable buttons 344 may be operatively connected to a pair of gear racks 346, wherein each gear rack 346 may have a curved shape as seen in FIG. 14. The detail of gear rack operation is best seen in FIG. 15 showing an internal part of the needle hub 340 with other parts removed for the clarity of the illustration.

Figure 15:
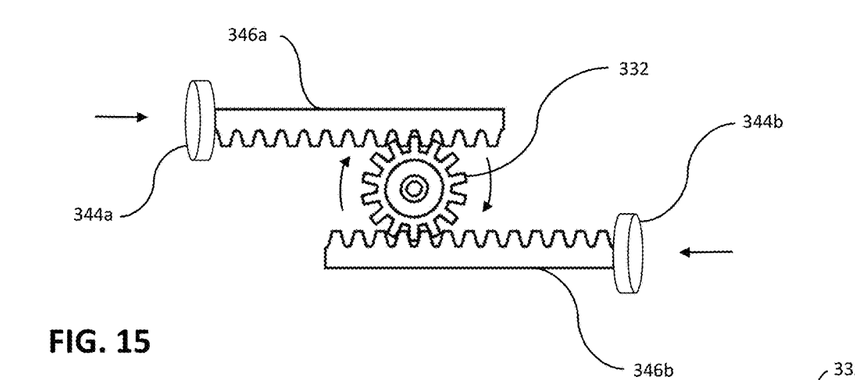
FIG. 15 shows a side view of the actuation mechanism inside the needle hub shown in FIG. 14.

Shown in FIG. 15 is a concept of rotating the gear pinion 332 by depressing the two buttons 344a and 344b and moving them together causing two gear racks 346a and 346b to move in the opposite directions towards each other and in turn causing limited rotation of the central gear pinion 332. The length of the gear racks 346, diameter of the gear pinion 332 and design of the gear teeth on all of these elements may be selected to assure rotation of the gear pinion 332 by about ½ of a turn when the buttons 344a and 344b are moved from an open initial state to a closed final position. The gear pinion 332 may be attached to the hollow needle 330 as seen in FIG. 16 so that the action of depressing two buttons 344 may be used to cause the gear racks 346 to rotate said gear pinion 332 and the hollow needle 330.

Figure 16:
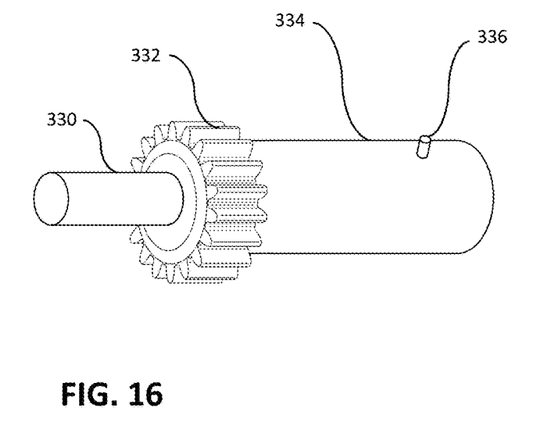
FIG. 16 shows a general view of the internal portion of the actuator of the needle hub according to the second embodiment of the invention.
Figure 17:
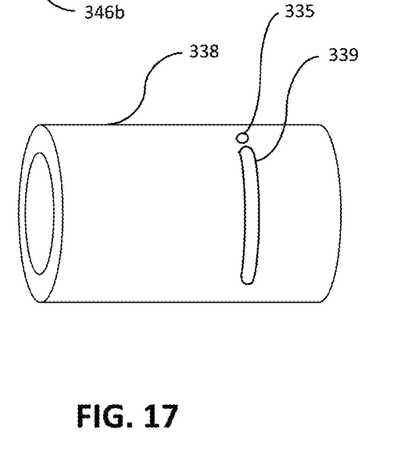
FIG. 17 shows the external cylinder configured to rotatably retain the internal portion shown in FIG. 16.

The entire rotary arrangement of the gear pinion 332 and the hollow needle 330 may be attached to an internal cylinder 334, which in turn may be rotatably retained inside the external cylinder 338 as seen in FIGS. 16 and 17. Similarly to the device 200, the pair of the internal cylinder 334 and the external cylinder 338 may be equipped with a pin 336 configured to slide inside the groove 339 so as to further limit the rotation of the hollow needle 330. In alternate embodiments, the groove 339 may have one or more sections positioned at an angle to the radial direction around the external cylinder 338 so as to cause the needle tip 320 to advance forward when the needle 330 is rotated around its longitudinal axis. The pin 336 may in some embodiments be spring-loaded to have a first position adapted to sliding inside the groove 339 and a second position to lock the internal cylinder 334 inside the external cylinder 338 when the rotation is complete and when the pin 336 has reached an opening 335 in the external cylinder 338. Other designs of the lock to automatically to automatically retain the hollow needle 330 in a rotated orientation upon completion of depressing of the two buttons 344 are also contemplated in this invention including various spring-loaded retention locks to prevent back motion of the gear racks 346 (not shown).

In use, the operator may grab the device 300 of the invention at the location of the buttons 344 and cause insertion of the hollow needle 330 through the skin. Upon reaching the target vessel (as may be evidenced by blood appearing in the visualization chamber 348), the buttons 344 may be depressed and moved closer together—causing the needle tip 320 rotation without changing the longitudinal position thereof inside the target vessel 10. Once the beveled tip 320 is rotated, the sheath 350 may be disengaged from the needle hub 340 and advanced further into the vessel 10. The needle 330 and the rest of the device 300 may then be removed.

Figure 18:
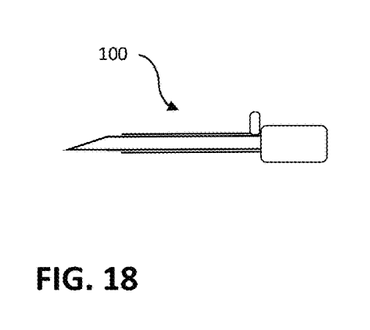
FIG. 18 shows a standard introducer catheter aligned with a novel adapter according to the second embodiment of the present invention.

FIG. 18 shows a variation of the second embodiment of the present invention designed to work with a standard introducer catheter 100. In this case, the adapter 360 may be configured to include an internal rotatable sleeve 362 configured to removably engage with the hub of the needle by having for example a compressible sleeve inside thereof. The rest of the design of the adapter 360 may be the same as described above for the device 300. In use, the adapter 360 may be first placed over the needle hub of the introducer catheter 100. The insertion and use of the assembly of the catheter 100 and the adapter 360 may then proceed along the lines described above.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. An introducer catheter for obtaining vascular access, the catheter comprising:
    a hollow needle extending from and rotatably supported within a needle hub, said hollow needle terminated with a beveled tip, and
    a flexible sheath extending from a sheath hub over said hollow needle to said beveled tip, said sheath hub removably retained on said needle hub,
    an actuator, further includes a rotating mechanism inside said needle hub, said rotating mechanism having a rotatable internal cylinder attached to said needle and a non-rotatable external cylinder attached to or formed together with said needle hub, wherein said internal cylinder is retained inside said external cylinder,
    wherein said actuator is configured to cause said hollow needle to rotate inside said needle hub about ½ of a turn upon activation thereof.

2. The catheter as in claim 1, wherein said rotating mechanism further comprising a pin configured to slide in a groove, said pin is attached to one of said internal cylinder or said external cylinder, said grove is formed in the other said external cylinder or said internal cylinder respectively, said groove configured to limit the rotation of the hollow needle by about ½ of a turn.

3. The catheter as in claim 2, wherein said groove is further configured to cause advancement of said hollow needle and said sheath forward by a distance from 1 mm to 3 mm.

4. The catheter as in claim 1, further comprising a torsion spring to cause rotation of said hollow needle upon actuating of the actuator, said torsion spring having a first end operatively connected to said internal cylinder and a second end operatively connected to said external cylinder, whereby said torsion spring urging said internal cylinder to rotate inside said external cylinder upon release thereof.

5. The catheter as in claim 4 further comprising a winding knob configured to wind up said spring to a preloaded state before use of said catheter.

6. The catheter as in claim 1, wherein said needle hub further comprises a transparent visualization chamber to detect a blood back event indicating a location of said beveled tip in a target vessel when blood enters said visualization chamber.

7. The catheter as in claim 1, wherein said actuator comprising a trigger.

8. An introducer catheter for obtaining vascular access, the catheter comprising:
   a hollow needle extending from a needle hub, said hollow needle terminated with a beveled tip, and
   a sheath extending from a sheath hub over said hollow needle to said beveled tip, said sheath hub removably retained on said needle hub,
   wherein said needle hub includes an actuator comprising a trigger and a spring-loaded rotating mechanism for turning said hollow needle, said rotating mechanism comprising an internal cylinder rotatably retained inside an external cylinder, said hollow needle is attached to said internal cylinder, said external cylinder is attached to or formed together with a needle hub housing, said rotating mechanism is further comprising a pin configured to slide in a groove, said pin is attached to one of said internal cylinder or said external cylinder, said grove is formed in said respectively another external cylinder or said internal cylinder, said groove configured to limit the rotation of the hollow needle by about ½ of a turn, said groove is further configured to cause advancement of said hollow needle and said sheath forward by a distance from 1 mm to 3 mm, said actuator configured to cause said hollow needle to rotate about ½ of a turn upon activation thereof, wherein said groove is further configured to cause said advancement forward of said hollow needle and said sheath in a second half of rotating of said hollow needle, while a first half of rotation of said hollow needle is caused by said actuator without forward motion thereof.

9. A method of obtaining vascular access comprising the steps of:
   a) providing an introducer catheter comprising a hollow needle extending from and rotatably supported within a needle hub, said hollow needle terminated with a beveled tip, and a sheath extending from a sheath hub over said hollow needle to said beveled tip, said sheath hub removably retained on said needle hub, wherein said needle hub includes an actuator and a rotating mechanism, said rotating mechanism comprising an internal cylinder rotatably retained inside an external cylinder, said internal cylinder attached to said needle and said external cylinder is attached to or former together with said needle hub,
   b) inserting said introducer catheter in a blood vessel at an oblique angle until blood is seen coming back through said needle,
   c) activating said actuator to cause said needle and said internal cylinder to rotate within said needle hub and said external cylinder by about ½ of a turn while maintaining position of said needle hub,
   d) disengaging said sheath hub from said needle hub and advancing said sheath forward into said blood vessel, and
   e) removing said needle and said needle hub while leaving said sheath in said blood vessel.

10. The method as in claim 9, wherein said step (c) further includes a step of advancing said hollow needle and said sheath forward by a distance from 1 mm to 3 mm.

* * * * *